United States Patent [19]

Savoca et al.

[11] Patent Number: 4,717,654
[45] Date of Patent: Jan. 5, 1988

[54] PROCESS FOR SOLID PHASE PLATELET ANTIBODY ASSAY

[75] Inventors: Kenneth V. Savoca, Edison; Valerie E. Macdonald, Branchville, both of N.J.

[73] Assignee: Akzo N.V., Arnhem, Netherlands

[21] Appl. No.: 622,350

[22] Filed: Jun. 19, 1984

[51] Int. Cl.[4] ............... G01N 33/535; G01N 33/566; G01N 33/554; G01N 33/537

[52] U.S. Cl. .................................... 435/7; 435/810; 436/501; 436/518; 436/519; 436/538; 436/808; 436/809; 436/811

[58] Field of Search ............... 436/501, 530, 518, 519, 436/531, 538, 540, 808, 809, 811; 435/7, 13, 21, 188, 810

[56] References Cited

U.S. PATENT DOCUMENTS

| | | | |
|---|---|---|---|
| 4,157,383 | 6/1979 | Sedlacek et al. | 424/3 |
| 4,287,087 | 9/1981 | Brinkhous et al. | 424/2 X |
| 4,469,787 | 9/1984 | Woods et al. | 435/7 |
| 4,492,751 | 1/1985 | Boguslaski et al. | 435/7 |
| 4,517,288 | 5/1985 | Giegel et al. | 435/7 |

OTHER PUBLICATIONS

Kunicki et al., *Blood*, 60, No. 1, (1982), pp. 54–58.
Hedge et al., *British Journal of Haemotology*, 1981, pp. 39–46.
Borzini et al., *Journal of Immunological Methods*, vol. 44, (1981), pp. 323–332.
Faig et al., *Blood*, vol. 60, No. 4, (1982), pp. 807–813.
Schiffer et al., *Blood*, vol. 61, No. 2, (1983), pp. 311–317.
Christie et al., *J. Clin. Invest.*, vol. 70, (1982), pp. 989–998.

*Primary Examiner*—Esther M. Kepplinger
*Attorney, Agent, or Firm*—William M. Blackstone

[57] ABSTRACT

Drug-induced thrombocytopenia can be detected via the use of an enzyme-linked immunospecific assay.

19 Claims, No Drawings

PROCESS FOR SOLID PHASE PLATELET ANTIBODY ASSAY

FIELD OF INVENTION

This invention relates to a solid phase immunoassay method for drug-induced thrombocytopenia. More particularly it relates to an enzyme-linked immunospecific assay (ELISA) adapted to detect drug-induced thrombocytopenia.

BACKGROUND OF THE INVENTION

In some individuals certain drugs can cause an immune reaction which results in thrombocytopenia. A causal relationship between thrombocytopenia and a specific drug cannot be assumed from clinical history either because the patient is taking multiple drugs or because an associated disorder is present which is known to be complicated by thrombocytopenia. The causal agent may be identified by rechallenging the patient with the suspected drug. This approach, however, has potential risks which may make it ethically unacceptable. Hence, an assay technique which detects the drug-dependent antibodies causing the adverse reaction is the preferred diagnostic approach.

Radioimmunoassay techniques have been utilized to detect drug-dependent antibodies. See, for example, Faig, Douglas and Karpatkin, Simon "A Cumulative Experience with a Simplified Solid-Phase Radioimmunoassay for the Detection of Bound Antiplatelet IgG, Serum Auto-, Allo-, and Drug-Dependent Antibodies," *J. Am. Soc. Hem.*, 60, (4): 807–813 (1982).

The technique disclosed involves the deposition of test platelets in wells of a microtiter plate. The platelets are washed and antihuman IgG (rabbit) is added to each platelet-coated microtiter well. After incubation for 1 hr. at room temperature, the wells are washed, treated with $^{125}$I-staphylococcal protein A, and again are incubated for one hour at room temperature. The wells are washed and the radioactivity of each well is then measured and compared to a control. While the technique is effective, it requires the use of radioactive substances with the attendant hazards.

Another technique utilized for the detection of platelet antibodies is an immunoenzymatic assay. Purified rabbit antihuman IgG antibodies are conjugated to beta-galactosidase with meta-maleimidobenzoyl-hydroxysuccinimide ester as a bifunctional reagent and or-thonitrophenyl-beta-galactopyranoside as a substrate to evaluate the enzymatic activity of labelled antiglobulin. The tests are carried out in the liquid phase and the antibodies are detected by immunofluorescence, optical density or other suitable measurements. See for example, Borzini, P. et al., "An Immunoenzymatic Assay for the Detection and Quantitation of Platelet Antibodies: The Platelet Beta-Galactosidase Test (PGT)," *J. Immuno. Meth.*, 14, 323–332 (1981).

Electroimmunoassay techniques have been applied to detection of platelet-associated IgG. See, for example, Kunicki, Thomas J., et al., "Direct Quantitation of Platelet-Associated IgG by Electroimmunoassay," *Blood* 60(1): 54–59 (1982). Electrophoresis has been utilized for the study of quinine and quinidine induced thrombocytopenia. See, for example, Christie, Douglas J., and Aster, Richard H., "Drug-Antibody-Platelet Interaction in Quinine- and Quinidine-Induced Thrombocytopenia," *J. Clin. Invest.*, 70(5): 989–999 (1982).

Enzyme-linked immunoabsorbent assay (ELISA) techniques have been applied to the detection of platelet antibodies. See Schiffer, Charles A., and Young, Virginia, "Detection of Platelet Antibodies Using a Micro-Enzyme-Linked Immunosorbent Assay (ELISA)," *Blood*, 61(2), 311–317 (1983). Lyophilized platelets are used in ELISA tests to detect platelet-associated IgG by a "sandwich" technique utilizing anti-human IgG conjugated to alkaline phosphatase. The results of the tests were quantified with p-nitrophenyl phosphate as the substrate using an automated micro ELISA reader.

Hegde, U. M., et al. have disclosed an ELISA test for detection of platelet associated IgG which comprises coating an antihuman IgG (AIgG) onto polystyrene, binding solublized platelet-associated IgG (PAIgG) to the AIgG, and subsequently measuring the PAIgG by using an enzyme conjugate and p-nitrophenyl phosphate as substrate. See Hegde, U. M., et al. "Enzyme Linked Immunoassay for the Detection of Platelet Associated IgG," *Brit. J. Hema.*, 48, 39–46 (1981).

U.S. Pat. No. 4,016,043 discloses an enzyme immunoassay (EIA) in which antihuman IgG bound to a polystyrene microtiter plate is treated with human serum or plasma. The treated plate is incubated for about 2 hours at 37° C. The wells of the microtiter plate are emptied and washed with a buffer of a pH of about 7.4.

This technique can be used for detection of Hepatitis B surface antigen wherein an antibody is bound to a polystyrene plate which is thereafter treated with serum or plasma. Horseradish peroxidase is added and the material is incubated to complete the reaction. The results are recorded as a colorimetric reading.

U.S. Pat. No. Re 31,006 discloses a similar EIA technique. It discloses as the substrates enzyme catalase, peroxidase, beta-glucuronidase, glucose-oxidase and galactose-oxidase.

U.S. Pat. No. 3,654,090 discloses a method for labeling an antigen or antibody with an enzyme. An example is a conjugate of human chorionic gonadotropin coupled with horseradish peroxidase.

SUMMARY OF THE INVENTION

Applicants have unexpectedly found that ELISA techiques can be applied to the determination of immune mediated drug-induced thrombocytopenia. The assay method of this invention comprises:

(a) contacting blood platelets with serum or plasma derived from a patient suspected of having a drug-induced thrombocytopenia and a drug suspected of causing the thrombocytopenia;

(b) incubating the platelets so treated for about 15 to about 25 minutes at a temperature of about 21° C. to about 24° C.;

(c) washing the treated platelets with a wash solution containing the drug and resuspending the platelets in the wash solution;

(d) contacting a solid support having bound thereto a specific binding protein with the resuspended platelets and incubating the reactants;

(e) decanting unbound platelets; and (f) measuring the bound platelets by:

(1) contacting the solid support having platelets bound thereto with an enzyme conjugate and incubating the reactants;

(2) removing unbound reactants;

(3) contacting the support plate with a substrate and incubating the reactants;

(4) determining the quantity of substrate acted upon by the enzyme conjugate; and (g) comparing with at least one of a standard value and a value derived by subjecting a drug-free control to steps (a) through (f).

In another embodiment, Applicants have developed a kit for the determination of drug-induced thrombocytopenia which contains (a) a water insoluble solid support having bound thereto a specific binding protein;

(b) an enzyme conjugate;

(c) a substrate; and (d) platelets.

By comparing the O.D. of the test sample with a control prepared in an identical manner, but without drug addition, the immunogenic effect of the suspected drug can be determined. The preferred enzyme conjugate is alkaline phosphatase-anti-IgG and the preferred substrate is para-nitrophenyl phosphate.

DETAILED DESCRIPTION OF INVENTION

This invention relates to the application of ELISA techniques to a diagnostic platelet antibody assay. In particular, it relates to a procedure for detecting a substance which is suspected of causing thrombocytopenia. Specifically, it relates to a method for detecting drug-induced thrombocytopenia and, in particular, quinine- or quinidine-induced thrombocytopenia.

In the practice of this invention lyophilized platelets are contacted with a serum or plasma derived from a patient suspected of having a drug-induced thrombocytopenia. The platelets are used as the immunoadsorbant for the antibodies which may exist in the serum or plasma. While fresh platelets may be utilized, it is preferred that lyophilized platelets be used to minimize background readings from antibodies already attached to the platelets. Human platelets normally have an antibody concentration of about 20 ng/$10^7$ platelets while the lyophilized platelets have an antibody concentration of about 1-3 ng/$10^7$ platelets.

Methods for preparing lyophilized platelets suitable for use in this invention are well known in the art. See, for example, U.S. Pat. No. 4,287,087. Fresh platelets are washed and fixed with formaldehyde, glutaraldehyde or (para)formaldehyde. The fixed platelets are lyophilized and stored in the dried state.

When reconstituted with purified water for use in the practice of this invention, the platelet suspension contains about $4.5 \times 10^5$ to about $5.5 \times 10^5$ platelets per microliter of suspension.

Drugs contemplated for use in the invention include those generally associated with drug-induced thrombocytopenia, for example, gold, quinine, quinidine, thyroxin, and sulphonamide derivatives. Quinine and quinidine are preferred. Mixtures of drugs may be present in the patients serum or plasma.

In carrying out the ELISA tests of this invention a solution of the drug suspected of causing thrombocytopenia is prepared. So that excessive dilutions are not required, a drug stock solution having a concentration of about 7 mM to about 10 mM is suitable for the purpose of this invention.

In carrying out the ELISA method of this invention the quantities of material utilized are not in themselves critical and may be varied within the scope and spirit of this invention.

In a preferred embodiment about 50 μl to about 150 μl of patient plasma is pipetted into a 1.5 ml microcentrifuge tube. To the tube is added about 15 to about 40 μl of drug stock solution and about 50 μl to about 150 μl of reconstituted platelets. The tube is gently vortexed and incubated for about 15 to about 25 minutes at about 21° C. to about 25° C.

During the incubation process if the patient's serum contains antibodies to the suspected drug, a drug-antibody-platelet complex will form. After incubation the tube is centrifuged and the supernatant liquid is discarded by carefully pipetting, taking care not to dislodge the platelet pellet.

The pellet is then washed using a platelet wash buffer containing the drug. The platelet wash buffer comprises about 0.020M to about 0.028M sodium phosphate, about 0.007M to about 0.010M disodium EDTA, about 0.10M to about 0.20M sodium chloride and about 0.750 to about 1.25% (w/v) bovine serum albumin.

To prepare a drug washing buffer about 2 to about 6 ml of drug stock solution is added to about 20 to about 35 ml of platelet wash buffer so that the drug is diluted about 1:10. About 100 μl of drug wash buffer is used for each pellet washing. The washed pellet is resuspended in the plate wash buffer.

The composition of the plate wash buffer is not critical. It can comprise only water and a nonionic surfactant. However, since in the practice of this invention the plate wash buffer will be used as a carrier for the enzyme conjugate it is preferred that the wash buffer have a pH of about 5.3 to about 8.6 in order to avoid deterioration of the enzyme conjugate. Preferably the pH of the plate wash buffer is about 7.0 to about 7.4.

A typical plate wash buffer comprises about 0.0175M to about 0.022M sodium phosphate, about 0.125M to about 0.175M sodium chloride; about 0.04% (v/v) to about 0.06% (v/v) of a nonionic surfactant and about 0.015% to about 0.022% (v/v) of sodium azide preservative.

In carrying out the drug-induced immunoassay of this invention dilution of the reaction complex must be performed to accurately determine the concentration of antibodies. If the level is too high it may result in optical density values beyond the limit of the particular ELISA reader utilized by the operator of the ELISA test utilized in the practice of this invention. To avoid this potential problem the drug-antibody treated platelets are diluted.

Typically, the dilution utilized in the practice of this invention may vary from 1:5 to about 1:100. In a preferred embodiment, two dilutions, 1:5 and 1:40 are used and tests are run in duplicate for each dilution.

The first step in quantifying the platelet associated drug-induced antibody is to react it with a specific binding protein which has been bound to an inert, insoluble support. The term "specific binding protein" as used in the specification and claims means one or more of a group of proteins that will specifically react with an antibody, antigen or hapten. Useful proteins include gamma globulins, immunoglobulins, and lectins. The specific binding protein of this invention preferably belongs to the immunoglobulin subclass known as IgG.

In the practice of this invention an antihuman IgG will generally be used as the specific binding protein.

The preparation and purification of specific binding proteins is well known in the art. A variety of antihuman IgG derived from, for example, goat or rabbit serum are readily available to the practitioner of ELISA type diagnostic tests.

The support to which the specific binding protein is based is a transparent, inert, water insoluble support capable of adsorbing or binding with the specific binding protein. Exemplary materials for such supports include hydrocarbon polymers such as polystyrene, polyethylene and polybutylene. Other suitable organic polymers include condensates, e.g., polyesters and polyamides; cellulose and cellulosic derivatives; and vinyl polymers, e.g., acrylates, methacrylates, vinyl chloride homopolymers, polyvinyl chloride-acrylate copolymers, copolymers of polystyrene, and the like.

A particularly effective form of the solid support surface is a test tube or microtiter plate well. The preferred solid support surface of this invention is a microtiter plate, since automated equipment is readily available for automatic ELISA reading.

The quantitative and/or qualitative amount of platelet-associated antibody is determined by treating the solid support medium with the drug/serum washed platelets. In carrying out the immunoassay of this invention the various dilutions of drug-antibody-platelet suspension are contacted with the solid support medium, for example, a microtiter plate coated with antihuman IgG. While the amount of platelet suspension used is not critical, it is preferred that about $1.0 \times 10^6$ to about $1.5 \times 10^7$ platelets are added to the well of the microtiter plate to be treated.

Microtiter plates of good quality suitable for use in the practice of this invention which have been coated with antihuman IgG are readily available and need not be prepared fresh for the ELISA tests of this invention. While any antihuman IgG may be utilized as the specific binding protein, typically goat or rabbit derived anti-IgG is used.

The solid support medium treated with the platelet suspension is incubated for about 3½ to 4½ hours at about 21° C. to about 24° C. During the incubation period platelets which have associated human IgG will be bound to the specific binding protein. The remaining platelets will be washed away during a rinsing of the solid support plate.

The qualitative and/or quantitative determination of bound platelet-associated antibodies is determined by contacting the treated support plate with a labelled material. The labelled material used in the immunoassay of this invention may be any conventional label, such as a radioactive isotope, an enzyme or a fluorimetric material. Regardless of how the labelling is accomplished, the labelled material serves as a tracer for the antibodies to be detected.

A particularly preferred method involves the use of enzyme conjugate wherein a specific binding protein is labelled with an enzyme. The term "enzyme conjugate" as used in the specification and claims means an immunological component covalently linked to one or more enzyme molecules. Such linking can be achieved by direct condensation or by using external bridging molecules in accordance with methods known to those skilled in the art. Thus the production of enzyme conjugates employing a covalent bond can be effected by reagents such as carbodiimides, diisocyanates, glutaraldehyde and bis-diazobenzidine.

The choice of enzyme that is to form a part of the conjugate is determined by properties such as specific binding activity (a high conversion rate increases the sensitivity of the test system) and the simplicity of determination of the enzyme. The simplest enzyme determinations are those in which an enzyme catalyzes a conversion in which colored reaction components are involved. Such colorimetric determinations can be automatic.

It is also possible to employ enzymes catalyzing those conversions in which reaction components are involved that can be determined spectrophotometrically or fluorimetrically.

Enzymes suitable for use in the practice of this invention include catalase, peroxidase, urease, glucose oxidase and alkaline phosphatase. Alkaline phosphatase is the preferred enzyme.

A solution of the enzyme conjugate is contacted with the treated support plate and incubated. The preferred length of time for incubation will depend on the concentration and activity of the enzyme conjugate and the temperature of incubation. For an alkaline phosphatase enzyme conjugate, the preferred incubation period is about 10 minutes to about 100 minutes, preferably about 15 to about 35 minutes, at about 21° C. to about 24° C. After the incubation is complete, the support plate is washed to remove unbound enzyme conjugate. The support plate is then treated with a substrate.

The term "substrate" as used in the specification and claims means a compound which can be acted upon by an enzyme to produce a reaction product. Where alkaline phosphatase is the enzyme, a preferred substrate is p-nitrophenyl phosphate ("PNPP"). The reaction product generated by the action of alkaline phosphatase on PNPP is p-nitrophenol, a yellow color body. Other substrates suitable for use with alkaline phosphatase include 4-methyl umbelliferyl phosphate, alpha-napthyl phosphate, flavone-3-diphosphate, and thymolphthaleine.

Additional enzyme-substrate pairs useful in the practice of this invention include horseradish peroxidase/orthophenylenediamine and peroxide, beta-glactosidase/ortho-nitrophenyl-beta-D-galactopyranoside, beta-galactosidase/umbelliferyl-beta-D-galactoside, glucose oxidase/orthodianisidine and horseradish peroxidase and the like.

After treatment with the substrate the support plate is incubated to bring about the production of substrate reaction product. The incubation period will depend on the particular enzyme-substrate pair utilized and the concentration of substrate in a substrate wash buffer with which the support plate is contacted. Where the enzyme-substrate pair is alkaline phosphatase-p-nitrophenyl phosphate the preferred incubation period is about 30 minutes to about 60 minutes at about 21° C. to about 24° C.

Preferably the substrate buffer comprises a purified water solution of about 8% to about 10% (v/v) of diethanolamine, about 0.4 mM to about 0.6 mM of magnesium chloride and about 0.0175 to about 0.022% (w/v) of sodium azide as a preservative.

The concentration of substrate in the substrate buffer is about 1 mg/ml to about 6 mg/ml. Preferably about 80 µl to about 200 µl of substrate buffer solution is added to each well of a microtiter plate which has been treated in accordance with the practice of this invention.

The amount of substrate reaction product, and, where a color body is the reaction product, the intensity of color produced will be direct functions of the amount of enzyme conjugate bound to the support plate. Hence, a measure of substrate reaction product is a measure of the drug-induced antibody which has been bound to the support plate.

The substrate reaction product is measured by determining the optical density of the reaction product formed in the wells of the microtiter plate. In the case of p-nitrophenyl phosphate the yellow reaction product, p-nitrophenol, is developed in the wells of the support plate. Where the solid support is a microtiter plate the optical density of the color body developed is determined using an ELISA reader at about 405 nm.

In order to have a control to reference against the reading so obtained, the entire procedure is repeated, but without the drug being included in the platelet wash buffer. A comparison of the optical density of the drug-containing system determines whether there is a drug-induced immune reaction. If there is no drug-induced immune reaction, the two optical density readings will be substantially the same. Otherwise the optical density of the system where there is a drug-induced immune reaction will be higher than that of the control.

In practice, the invention generally involves comparing the values obtained from treated (i.e., drug-containing) platelets to the values obtained from control platelets and noting significant differences therein. It has been found that, in general, a more significant difference in values corresponds to a greater likelihood that the drug being investigated is causative of the drug-induced thrombocytopenia.

The invention has been described as assay means for comparing a patient's sample against a negative control, i.e., one which does not contain significant amounts of the suspected drug. However, the determination of the quantity of substrate can be made by standard techniques, for example, by comparison to a standard curve prepared from analysis of IgG as well as by the use of other suitable controls or standards.

The advantages of the instant invention may be more readily appreciated by reference to the following examples.

All percentages throughout the disclosure, including the examples, are based upon weight, unless otherwise indicated.

EXAMPLE I

This example demonstrates the utility of this invention for the detection of quinine induced thrombocytopenia.

A plate wash buffer ("PWB") was prepared having the following composition:

| | |
|---|---|
| Sodium phosphate | 0.02 M |
| Sodium chloride | 0.15 M |
| Surfactant[(1)] | 0 05% (w/v) |
| Sodium azide | 0.02% (w/v) |
| Purified water | Q.S. |

[(1)]an ethoxylated polymer (Tween 20) was used as the surfactant.

A Platelet Wash Buffer was prepared having the following composition:

| | |
|---|---|
| Sodium phosphate | 0.026 M |
| Disodium ethylene diamine-tetraacetic acid | 0.009 M |
| Sodium chloride | 0.15 M |
| Bovine serum albumin | 1% (w/v) |
| Purified water | Q.S. |

The plate wash buffer and platelet wash buffer should be prepared fresh but may be stored at about 2° to about 8° C. if prepared in advance.

A substrate buffer was prepared having the following composition:

| | |
|---|---|
| Diethanolamine | 9.7% (v/v) |
| Magnesium chloride | 0.5 mM |
| Sodium azide | 0.02% (w/v) |
| Purified water | 8 ml |
| p-nitrophenyl phosphate | 40 mg |

The substrate buffer is preferably prepared fresh but may be stored at −20° C. for one month if freezing-thawing is avoided. At room temperature the buffer must be used within one hour after preparation.

Lyophilized platelets which were previously prepared from type O blood are reconstituted using purified water. The platelet concentration in the platelet solution is about $5 \times 10^5$ platelets in a microtiter.

A sample of blood is withdrawn from a patient who is believed to be suffering from quinine-induced immune thrombocytopenia. The blood is centrifuged and the platelet free plasma is carefully pipetted and reserved for use.

A drug stock solution is prepared by dissolving 17.9 mg. of quinine.HCl.2H$_2$O into 5 ml deionized water. This solution has a quinine concentration of 9 mM. A drug washing buffer is prepared by adding 4 ml of drug stock solution to 28 ml of platelet wash buffer which has been previously diluted 1:10.

100 μl of plasma is pipetted into each of two plastic 1.5 ml micro-centrifuge tubes. The tubes are labelled "A" and "B".

25 μl of 9 mM drug stock solution was added to tube A. 25 ml platelet wash buffer (without drug) was added to tube B. After mixing 100 μl of reconstituted platelets was added to each tube. The tubes were gently vortexed and incubated at about 23° C. for twenty minutes. Each tube was mixed gently after a ten minute interval. Both tubes were centrifuged at 200×g for ten minutes and the supernatant was discarded by carefully pipetting without dislodging the platelet pellet.

About 100 μl of drug wash buffer was added to tube A and about 100 μl of platelet wash buffer was added to tube B. The platelets were resuspended by trituration with a pipette. The washed platelets were centrifuged and washed two more times in the same manner.

To each of the tubes A and B was added 0.5 ml plate wash buffer. Each sample was triturated and vortexed. The test sample (A) and the control (B) are each diluted 1:5 and 1:40. For the 1:5 dilution 100 μl of tube A or B is added to 400 μl of plate wash buffer. For the 1:40 dilution 50 μl of Tube A or B is added to 1.95 ml of plate wash buffer.

100 μl of each dilution was pipetted into the wells of a microtiter plate having anithuman-IgG bound to its surface. The plate was covered with plastic film to prevent evaporation and incubated at 23° C. for 4 hours. The solutions were drained from the microtiter plate, the plate was washed three times with plate wash buffer and drained of liquid. About 100 μl of a solution of alkaline phosphatase-antihuman-IgG conjugate in plate wash buffer was added to each test well and the plate was incubated at about 23° C. for 30 minutes. At the end of the incubation period the solution was drained from the plate and the plate was washed three times with plate wash buffer.

About 100 μl of substrate in buffer was added to each test well and the plate was incubated for 30 minutes at 23° C. The optical density of each of the test wells was measured using an ELISA reader. The optical density (O.D.) of the 1:5 dilution of the control was 0.257 while the optical density of the test specimen was 0.655. It was concluded that, based on the difference in O.D. values between the two readings, the patient's thrombocytopenia was drug-induced.

Those skilled in the art will appreciate that commercially available enzyme conjugates will vary from lot to lot and a standard dilution of known strength must be prepared. This can be accomplished by first arbitrarily selecting an IgG nanogram count which is to correlate with an O.D. of 1.0. That number of nanograms of human IgG, for example 128 ng, is added to each of about 6 to about 10 wells of the microtiter plate. After incubation for 4 hours at about 21° C. to about 23° C., the plate is washed and various dilutions of enzyme conjugate; for example 1:25, 1:50, 1:75, 1:100, and so forth; are added to each of the wells.

The test procedure described above is followed and the dilution which corresponds to an O.D. of 1.0 is the dilution selected for use in the drug immune thrombocytopenia assays of this invention. A new dilution value must be determined each time a new sample of enzyme conjugate is used.

EXAMPLE II

Example I was repeated except that quinidine was substituted for quinine as the drug. To prepare a 9 mM drug stock solution 18.6 mg of quinidine.HCl.H$_2$O was added to 5 ml deionized water. The optical density of the 1:5 dilution of the control was 0.262 and the optical density of the 1:5 dilution of the test specimen was 1.246. Again, the results indicate that the patient's thrombocytopenia was drug-induced.

Reasonable variations, such as those which would occur to a skilled artisan, can be made herein without departing from the scope of the invention. Such variations are not to be regarded as a departure from the spirit or scope of the invention and all such modifications are intended to be included within the scope of the claims.

What is claimed is:

1. A method for detecting drug-induced thrombocytopenia which comprises:
   (a) contacting blood platelets with a serum or plasma sample derived from a patient suspected of having a drug-induced thrombocytopenia and a drug suspected of causing the thrombocytopenia;
   (b) incubating the platelets so treated for about 15 to about 25 minutes at a temperature of about 21 degrees C. to about 24 degrees C. to form a drug-antibody-platelet complex with any antibodies to said drug in said patient sample;
   (c) washing the treated platelets with a wash solution containing said drug and resuspending the platelets in the wash solution;
   (d) contacting a solid support having first bound thereto one or more of a group of immunoreactive proteins that will specifically react with a human antibody with the resuspended platelets and incubating these to bind any platelets having human antibody or hapten thereon to said solid support;
   (e) decanting the platelets that remain unbound in step (d);
   (f) measuring the platelets that become bound in step (d) by:
      (1) contacting the solid support having platelets bound thereto with an immunological component that is immunoreactive with a human antibody, said immunological component having a detectable label, and incubating these;
      (2) removing unbound immunological component by means of washing;
      (3) measuring the quantity of label immobilized on said support; and
   (g) determining whether the platelets that become bound in step (d) are part of the drug-antibody-platelet complex formed in step (b), indicating thrombocytopenia, by comparing the determined quantity of label in step (f)(3) with a standard curve and/or a quantity derived by repeating steps a) through (f) with the proviso that no drug is added in step (a) and that a wash solution containing no drug is used in step (c), whereby the presence of said complex is evidenced by a higher quantity of label determined for the patient sample than given by the standard curve or determined by repeating steps (a) through (f) without adding the drug in steps (a) and (c).

2. The process according to claim 1 wherein the detectable label on the immunological component of (f)(1) is alkaline phosphatase and the immunological component is antihuman IgG, the solid support of (d) is a microtiter plate, the protein of (d) is antihuman-IgG and the quantity of the label is determined by adding a substrate for the detectable label.

3. The process according to claim 2 wherein the drug is quinine.

4. The process according to claim 2 wherein the drug is quinidine.

5. The process according to claim 2 wherein the substrate is p-nitrophenyl phosphate.

6. The process according to claim 1 wherein the platelets are reconstituted lyophilized human platelets.

7. The process according to claim 1 wherein the solid support of (f)(1) is a microtiter plate and the specific binding protein is antihuman-IgG.

8. The process according to claim 1 wherein the platelets are incubated in contact with the solid support in step (d) for about 3½ to about 4½ hrs at about 21° C. to about 24° C.

9. The process according to claim 2 wherein the platelet treated solid support obtained in step (d) is contacted with the labeled immunological component and incubated for about 15 minutes to about 35 minutes at about 21° C. to about 24° C.

10. The process according to claim 2 wherein the substrate is contacted with the support plate/labeled immunological component obtained in step (f)(1) and incubated for about 30 minutes to about 60 minutes at a temperature of about 21° C. to about 24° C.

11. An immunoassay kit for assaying drug-induced cytopenia which comprises, in separate containers:
   (a) a water insoluble solid support having bound thereto one or more of a group of immunoreactive proteins that will specifically react with a human antibody;
   (b) an immunological component that is immunoreactive with a human antibody covalently linked to one or more enzyme molecules;

(c) an enzyme substrate; and
(d) platelets.

12. The assay kit according to claim 11 wherein the specific binding protein is antihuman-IgG.

13. The assay kit according to claim 11 wherein the enzyme of 11(b) is an alkaline phosphatase.

14. The assay kit according to claim 13 wherein the substrate of 12(c) is p-nitrophenyl phosphate.

15. The assay kit of claim 11 wherein the platelets of 12(d) are lyophilized human blood platelets.

16. The assay kit according to claim 11 which additionally contains at least one substance which is suspected of causing thrombocytopenia.

17. The assay kit according to claim 16 wherein the substance is selected from the group consisting of: gold, quinine, quinidine, thyroxin, and sulphonamide derivatives.

18. A method for detecting drug-induced thrombocytopenia which comprises:
(a) preparing a drug-containing sample by contacting blood platelets with a serum or plasma sample derived from a patent suspected of having a drug-induced thrombocytopenia and a drug suspected of causing the thrombocytopenia;
(b) preparing a control sample by contacting blood platelets with serum or plasma from said patient in the absence of said drug;
(c) separately incubating the samples of steps (a) and (b) for about 15 to about 25 minutes at a temperature of about 21 degrees C. to about 24 degrees C. to produce drug-containing treated platelets and control platelets, respectively, whereby antibodies to said drug in the sample derived from a patient will form a drug-antibody-platelet complex;
(d) washing the drug-containing treated platelets with a washing solution containing the drug and resuspending the platelets;
(e) washing the control platelets with a wash solution containing no drug and resuspending the platelets;
(f) separately subjecting the products of steps (d) and (e) to an assay which comprises:
(g) contacting a solid support having first bound thereto one or more of a group of immunoreactive proteins that will specifically react with a human antibody with the resuspended platelets and incubating these to bind any platelets having human antibody thereon to said solid support;
(h) decanting unbound platelets that remain unbound in step (g); and
(i) measuring the bound platelets that become bound in step (g) by:
(1) contacting the solid support having platelets bound thereto with an immunological component that is immunoreactive with a human antibody, said immunological component being covalently linked to one or more enzyme molecules, and incubating these;
(2) removing unbound immunological component;
(3) contacting the solid support with a substrate for the beforementioned enzyme and incubating these; and
(4) determining the quantity of substrate acted upon by the enzyme; and,
(j) comparing the determination obtained using the drug-containing platelets and the determination obtained using the control platelets, wherein the presence of thrombocytopenia is evidenced by a higher OD value as compared with that of the control platelets.

19. The process according to claim 18 wherein the drug of (a) is selected from the group consisting of: quinine and quinidine.

* * * * *